United States Patent
Shapira (10) Patent No.: US 12,018,312 B2
(45) Date of Patent: Jun. 25, 2024

(54) PURIFICATION OF MAGNESIUM LACTATE FROM FERMENTATION BROTHS HAVING HIGH AMOUNTS OF IMPURITIES

(71) Applicant: TripleW Ltd., Netanya (IL)

(72) Inventor: Tal Shapira, Even Yehuda (IL)

(73) Assignee: TripleW Ltd., Netanya (IL)

(*) Notice: Subject to any disclaimer, the term of this patent is extended or adjusted under 35 U.S.C. 154(b) by 298 days.

(21) Appl. No.: 17/295,415

(22) PCT Filed: Nov. 25, 2019

(86) PCT No.: PCT/IL2019/051287
§ 371 (c)(1),
(2) Date: May 19, 2021

(87) PCT Pub. No.: WO2020/110108
PCT Pub. Date: Jun. 4, 2020

(65) Prior Publication Data
US 2021/0395788 A1  Dec. 23, 2021

Related U.S. Application Data

(60) Provisional application No. 62/771,185, filed on Nov. 26, 2018.

(51) Int. Cl.
*C12P 7/56* (2006.01)
(52) U.S. Cl.
CPC ....................... *C12P 7/56* (2013.01)
(58) Field of Classification Search
None
See application file for complete search history.

(56) References Cited

U.S. PATENT DOCUMENTS

| 3,429,777 | A | * | 2/1969 | Eli | ............................ | C12P 7/56 |
| | | | | | | 562/513 |
| 7,705,180 | B2 | | 4/2010 | Van Krieken | | |
| 9,689,007 | B2 | | 6/2017 | Baets | | |
| 2014/0012041 | A1 | | 1/2014 | Horiguchi | | |
| 2017/0218408 | A1 | | 8/2017 | Baets | | |

FOREIGN PATENT DOCUMENTS

| CN | 101979368 A | 2/2011 |
| CN | 105018538 A | 11/2015 |
| CN | 106083565 A | 11/2016 |
| EP | 1765757 B1 | 5/2009 |
| EP | 2604696 A1 | 6/2013 |
| JP | H08337552 A | 12/1996 |
| WO | 0017378 A2 | 3/2000 |
| WO | 2006124633 A1 | 11/2006 |
| WO | 2013093028 A1 | 6/2013 |
| WO | 2016016233 A1 | 2/2016 |
| WO | 2017178426 A1 | 10/2017 |
| WO | 2017207501 A1 | 12/2017 |

OTHER PUBLICATIONS

Datta and Henry (2006) Lactic acid: recent advances in products, processes and technologies—a review. Journal of Chemical Technology & Biotechnology 81(7): 1119-1129.
Huang et al., (2004) A hollow-fiber membrane extraction process for recovery and separation of lactic acid from aqueous solution. Appl Biochem Biotechnol 113-116: 671-688.
Joglekar et al., (2006) Comparative assessment of downstream processing options for lactic acid. Separation and Purification Technology 52(1): 1-17.
Wang et al., (2015) Efficient magnesium lactate production with in situ product removal by crystallization. Bioresour Technol 198: 658-663.

* cited by examiner

*Primary Examiner* — Christian L Fronda
(74) *Attorney, Agent, or Firm* — Rodney J. Fuller; BOOTH UDALL FULLER, PLC (57) ABSTRACT

A process for efficient purification of magnesium lactate from fermentation broths derived from non-homogeneous feedstocks that contain soluble and insoluble impurities is provided. The fermentation broth, having high amounts of impurities and containing magnesium lactate in a soluble form, is separated from insoluble impurities, concentrated to particularly high concentrations of the magnesium lactate at elevated temperatures, and subsequently cooled by gradual and controlled cooling such that magnesium lactate crystals of high purity are formed.

19 Claims, 6 Drawing Sheets

PURIFICATION OF MAGNESIUM LACTATE FROM FERMENTATION BROTHS HAVING HIGH AMOUNTS OF IMPURITIES

FIELD OF THE INVENTION

The present invention relates to methods for the purification of magnesium lactate from fermentation broths having high amounts of impurities including soluble and insoluble impurities and containing magnesium lactate in a soluble form, said methods comprising the steps of separation of impurities, concentration, crystallization and purification.

BACKGROUND OF THE INVENTION

Lactic acid is the most widely occurring hydroxycarboxylic acid (Joglekar, H. G., et al. "Comparative assessment of downstream processing options for lactic acid." Separation and Purification Technology 52.1 (2006): 1-17). It is a versatile chemical with applications in the food, chemical, pharmaceutical and cosmetic industries (Huang, H et al. (2004) A Hollow-Fiber Membrane Extraction Process for Recovery and Separation. Biochemistry and Biotechnology, 113). This naturally occurring organic acid can be produced by chemical synthesis or microbial fermentation. It is already present in many foods either naturally or as a product of in situ microbial fermentation (e.g., yogurt, buttermilk and many other fermented foods) (Datta, R., et al. (2006) Lactic acid: recent advances in products, processes and technologies—a review, 1129 (May), 1119-1129).

When produced by microbial fermentation, during the fermentation process the pH in the fermenter typically needs to be maintained at 5-7. Due to the production of lactic acid the pH decreases, which is not ideal for the productivity of the microorganisms. Adding bases such as ammonium-, sodium-, potassium-, magnesium- or calcium hydroxide can maintain the pH by neutralizing the lactic acid, with the formation of a lactate salt. To obtain crude lactic acid, a re-acidification step with, e.g., sulfuric acid is typically carried out.

Lactic acid fermentation based on renewable resources, compared to traditional petrochemical production, has gained increasing attention over the years. However, in order to compete with the traditional chemical production routes, the costs of bio-based lactic acid production need to be optimized. Approximately 60-80% of the production costs result from downstream processes, including the purification, concentration, and separation of the lactic acid/lactate salt from the fermentation broth. Additionally, reducing or eliminating the production of by-products (such as salts) is desired.

Various methods have been previously proposed for recovering and purifying lactic acid and/or lactate salts from fermentation broths.

For example, a process for magnesium lactate purification based on crystallization is described in Wang Yong, et al, "Efficient magnesium lactate production with in situ product removal by crystallization", Bioresource technology 198 (2015): 658-663. The crystallization was conducted at 42° C. without seed crystal addition. The fermentation medium used in the fermentor contained yeast extract, glucose, NaCl, sodium acetate, triammonium citrate, $KH_2PO_4$, $MgSO_4.7H_2O$ and $MnSO_4.7H_2O$. The product concentration, productivity and yield of fermentation coupled with in situ product removal (ISPR) reached 143 g $L^{-1}$, 2.41 g $L^{-1}h^{-1}$ and 94.3%, respectively.

U.S. Pat. No. 9,689,007 depicts a method for producing lactate or lactic acid from "low sugar" plant extracts via fermentation, comprising providing a fermentation medium that includes at least 25 wt. % of a plant extract containing fermentable carbohydrates, and fermenting the fermentation medium by means of a lactic acid producing microorganism in the presence of a caustic magnesium salt to provide a fermentation broth containing at the most 9.5 wt. % magnesium lactate at the end of fermentation, the magnesium lactate being in soluble form during and at the end of fermentation. To achieve a magnesium lactate concentration in the fermentation broth at the end of fermentation which is at most 9.5 wt. %, the fermentation medium comprising the plant extract preferably contains fermentable carbohydrates in a concentration of at most 9.5 wt. %.

US Publication No. 2014/0012041 depicts a method of producing a lactic acid salt comprising: subjecting an aqueous lactic acid salt solution comprising a formic acid salt in an amount of not less than 7.0% by weight with respect to said lactic acid salt to crystallization, and recovering said lactic acid salt. The lactic acid salt concentration in said aqueous lactic acid salt solution is 10.0 to 30.0% by weight.

US Publication No. 2017/0218408 depicts a method for preparing a fermentation product including lactic acid, the method including: a) treating a lignocellulosic material, being in a particulate state and has an average particle size of from 0.1 to 250 mm, with caustic magnesium salt in the presence of water to provide treated aqueous lignocellulosic material; b) saccharifying the treated aqueous lignocellulosic material in the presence of a hydrolytic enzyme to provide a saccharified aqueous lignocellulosic material comprising fermentable carbohydrate and a solid lignocellulosic fraction; c) simultaneously with step b), fermenting the saccharified aqueous lignocellulosic material in the presence of both a lactic acid forming microorganism and caustic magnesium salt to provide an aqueous fermentation broth comprising magnesium lactate and a solid lignocellulosic fraction; d) recovering magnesium lactate from the broth, wherein the saccharification and the fermentation are carried out simultaneously. The feedstock for the process of US Publication No. 2017/0218408 is a lignocellulosic material, which includes materials containing cellulose, hemicellulose and lignin, such as may be derived from plant biomass. Preferred lignocellulosic materials are selected from the group consisting of: wheat straw; sugarcane bagasse; corn stover; and, mixtures thereof.

WO Publication No. 2017/178426 depicts a fermentation process for producing magnesium lactate from a carbon source comprising the steps of—providing a fermentation medium comprising a fermentable carbon source in a fermentation reactor, —fermenting the fermentation medium by means of a lactic acid producing microorganism in the presence of an alkaline magnesium salt to provide a fermentation broth comprising magnesium lactate, and—recovering solid magnesium lactate from the magnesium lactate containing fermentation broth, wherein during at least 40% of the operating time of the fermentation process, the concentration of solid magnesium lactate in the fermentation broth is maintained in the range of 5-40 vol. %, calculated as solid magnesium lactate crystals on the total of the fermentation broth. Examples of fermentable carbon sources are $C_5$ sugars, $C_6$ sugars, oligomers thereof (e.g. dimeric $C_{12}$ sugars) and/or polymers thereof.

WO Publication No. 2017/207501 depicts a method for separating biomass from solid fermentation product wherein a slurry comprising biomass and solid fermentation product is provided to the top of a biomass separator unit and an aqueous medium is provided to the bottom of a biomass separator unit, while a product stream comprising solid fermentation product is withdrawn from the bottom of the biomass separator unit and a waste stream comprising biomass is withdrawn from the top of the biomass separator unit. The solid fermentation product is a fermentation product which is present in the aqueous medium in a concentration above its saturation concentration, and may be a crystalline product or an amorphous product.

The above-described purification methods are designed for fermentation broths derived from substantially homogenous biomass-based feed streams having low soluble and insoluble impurities content. There is a need, however, to utilize more available and less expensive non-homogeneous feedstocks for fermentation, such as mixed food waste from municipal, industrial and commercial origin. These non-homogeneous feedstocks contain impurities such as salts, lipids, proteins, color components and inert materials. Fermentation broths derived from said non-homogeneous feedstocks cannot be effectively processed by the currently available methods in order to obtain a pure magnesium lactate product in a cost-effective manner.

There remains an unmet need for simple, cost-efficient methods with high recovery yields for the purification and isolation of magnesium lactate from fermentation broths derived from non-homogeneous feedstocks having high amounts of mixed impurity content.

SUMMARY OF THE INVENTION

The present invention provides processes for the separation and purification of magnesium lactate from complex fermentation broths having high amounts of impurities, comprising the steps of separation of insoluble impurities, concentration, crystallization and purification. The use of complex fermentation broths, advantageously based on waste material, renders the process both economically and environmentally beneficial.

The invention is based in part on the unexpected finding that magnesium lactate crystals having a purity of over 85%, over 92%, or over 95% can be obtained from a complex, non-homogeneous, fermentation broth by a small number of steps of a purification process. In the process the complex, non-homogeneous, fermentation broth, having high amounts of impurities and containing magnesium lactate in a soluble form, is separated from insoluble impurities, concentrated to particularly high concentrations of the magnesium lactate at elevated temperatures, and subsequently cooled by gradual and controlled cooling. Surprisingly, even though the fermentation broth contained high amounts of impurities, the process yielded highly pure crystals in a cost-effective manner.

Purification methods known in the art are designed for fermentation broths derived from substantially homogenous biomass-based feed streams, containing relatively low amounts of soluble and insoluble impurities. These known methods are not cost effective or suitable for fermentation broths derived from non-homogeneous and complex feedstocks having high concentrations of soluble and insoluble impurities.

The present inventors have found a simple and economic process for obtaining high purity magnesium lactate crystals from a non-homogeneous fermentation broth. The fermentation broth is obtained from feedstocks comprising high concentrations of soluble and insoluble impurities from municipal, industrial and commercial origin. The insoluble impurities can contain organic-based impurities and inorganic-based impurities.

Non-limiting examples of insoluble organic-based impurities contain: microorganisms, fats and oils, lipids, aggregated proteins, bone fragments, hairs, precipitated salts, cell debris and residual unprocessed waste (such as food shells, seeds, food insoluble particles and debris, etc.). Non-limiting examples of insoluble inorganic-based impurities contain: plastics, glass, residues from food packaging and sand. Non-limiting examples of soluble impurities contain: seed fragments, salts, color components, etc.

The process of the present invention comprises, according to some embodiments, maintaining the fermentation broth at a temperature of about 45-75° C., in which the magnesium lactate is in a soluble form, during the initial steps of separation and concentration, such that substantially no crystals are formed before the fermentation broth is clarified from the insoluble impurities and concentrated to a desired concentration.

The present inventors have found that formation of magnesium lactate crystals during the fermentation process of non-homogeneous feedstocks (such as mixed food wastes from municipal, industrial and commercial origin) and prior to clarification and concentration, results in low purity magnesium lactate crystals having high amounts of soluble and insoluble impurities incorporated within (such as color components), and undesired crystalloid polymorphs. Said low purity magnesium lactate crystals will require additional processing steps and machinery for their purification, and therefore are not cost effective or desirable.

According to some embodiments, the process of the present invention comprises concentrating a fermentation broth to a desired concentration of about 180 g/L-220 g/L of lactate; crystallizing said broth under controlled cooling in order to obtain magnesium lactate crystals; and collecting the obtained crystals. The liquid remaining after collection of the crystals (referred to herein as 'mother liquor') may be recycled and subjected to additional crystallization(s). Thus, in some embodiments, the process of the present invention further comprises concentrating the mother liquor and performing at least one additional crystallization. Without wishing to being bound by theory or mechanism of action, it is contemplated that the high purity of the obtained magnesium lactate crystals was achieved due to the concentration of the fermentation broth, and the conditions of the crystallization step, such as temperatures, pH and cooling rates, which enabled the magnesium lactate to form crystals which were densely packed and were able to repel soluble impurities (such as color components), resulting in magnesium lactate crystals having a high purity of over about 93%.

The present inventors have found that concentrating the fermentation broth to a different concentration (below or above the desired concentration presented herein above) and/or utilizing different uncontrolled conditions for the crystallization, results in low purity magnesium lactate crystals having high amounts of soluble and insoluble impurities incorporated within. The obtained low purity magnesium lactate crystals will require additional processing steps and machinery for their purification, and therefore are not cost effective or desirable.

The present invention therefore provides improved methods for obtaining magnesium lactate from non-homogeneous fermentation broths using feedstocks comprising high concentrations of soluble and insoluble impurities. Said improved methods are simple, cost effective and result in high yields. The insoluble impurities may be removed before or after fermentation to produce lactate. According to some embodiments separating a major part of the impurities (the insoluble impurities) prior to fermentation is more economical. In some embodiments, after fermentation and lactate production the remaining impurities may be removed via microfiltration Thus, according to a first aspect, there is provided a process for the separation and purification of magnesium lactate from a fermentation broth, comprising the steps of:
a) providing a clarified fermentation broth from which insoluble impurities have been removed comprising magnesium lactate in a soluble form being the result of a fermentation process, the fermentation broth being at a temperature of about 45° C. to about 75° C.;
b) concentrating the clarified broth from step (a) to a concentration of about 150 g/L to about 220 g/L of lactate;
c) performing at least one cooling crystallization of the concentrated clarified broth from step (b) to obtain magnesium lactate crystals; and
d) collecting the magnesium lactate crystals obtained.

In some embodiments, the insoluble impurities comprise at least one of insoluble organic-based impurities, insoluble inorganic based impurities and soluble impurities.

In some embodiments, the fermentation broth at step (a) is at a temperature of about 55° C. to about 65° C.

In some embodiments, the separation of insoluble impurities comprises at least one technique selected from: filtration, centrifugation, flotation, sedimentation, flocculation and decantation. In some embodiments, the separation of insoluble impurities comprises centrifugation. In some embodiments, the separation of insoluble impurities further comprises microfiltration. In some embodiments, the separation of insoluble impurities comprises centrifugation and microfiltration.

In some embodiments, the concentration at step (b) is performed by evaporation, nanofiltration, reverse osmosis, or combinations thereof. In some embodiments, the broth at step (b) is concentrated to a concentration of about 160 g/L to about 220 g/L of lactate. In some embodiments, the broth at step (b) is concentrated to a concentration of about 170 g/L to about 220 g/L of lactate. In some embodiments, the broth at step (b) is concentrated to a concentration of about 180 g/L to about 220 g/L of lactate.

In some embodiments, at step (c) the at least one cooling crystallization begins at a first temperature selected from the range of about 50 to about 75° C. In some embodiments, at step (c) the at least one cooling crystallization begins at a first temperature selected from the range of about 50 to about 70° C. In some embodiments, at step (c) the at least one cooling crystallization begins at a first temperature selected from the range of about 50 to about 65° C.

In some embodiments, at step (c) the at least one cooling crystallization step ends at a second temperature selected from the range of about 10 to about 1° C. In some embodiments, at step (c) the at least one cooling crystallization ends at a second temperature selected from the range of about 6 to about 2° C.

In some embodiments, at step (c) the cooling rate of the at least one cooling crystallization is in the range of about 10 to about 0.5° C./h. In some embodiments, at step (c) the cooling rate of the at least one cooling crystallization is in the range of about 5 to about 1° C./h.

In some embodiments, at step (c) before the at least one cooling crystallization, the pH of the concentrated clarified broth is in the range of about 6 to about 7.

In some embodiments, the obtained magnesium lactate crystals at step (d) are separated from the remaining liquid by a method selected from microfiltration and nanofiltration.

In some embodiments, the remaining liquid from step (d) undergoes concentration, followed by at least one additional crystallization, in order to obtain additional magnesium lactate crystals. In some embodiments, the additional obtained magnesium lactate crystals are separated from the liquid. In some embodiments, the obtained magnesium lactate crystals are combined with the additional obtained magnesium lactate crystals, thus forming combined magnesium lactate crystals.

In some embodiments, the process further comprises step (e): washing and/or purifying the obtained magnesium lactate crystals or the combined magnesium lactate crystals. In some embodiments, step (e) comprises washing and/or purifying the obtained magnesium lactate crystals or the combined magnesium lactate crystals, utilizing an organic solvent selected from the group consisting of: ethanol, propanol, isobutanol, cyclohexane, acetone, ethyl acetate and combinations thereof. In some embodiments, step (e) comprises washing and/or purifying the obtained magnesium lactate crystals or the combined magnesium lactate crystals with an aqueous solution. In some embodiments, the solvent or the solution in step (e) has a specific temperature selected from about 0.5 to about 8° C.

In some embodiments, step (e) further comprises at least one polishing step, selected from extraction, microfiltration, nanofiltration, active carbon treatment, distillation, drying and grinding. In some embodiments, step (e) further comprises packaging for transportation purposes.

It is to be understood that any combination of each of the aspects and the embodiments disclosed herein is explicitly encompassed within the disclosure of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

DETAILED DESCRIPTION OF THE INVENTION

The present invention provides a process for the separation and purification of magnesium lactate crystals from a non-homogeneous fermentation broth comprising magnesium lactate in a soluble form, said broth is obtained from feedstocks comprising high concentrations of soluble and insoluble impurities from municipal, industrial and commercial origin. Said process comprises the steps of separation of insoluble impurities, concentration, crystallization and purification.

The insoluble impurities may be removed before or after fermentation to produce lactate. According to some embodiments, separating a major part of the insoluble impurities is carried out after fermentation. For example, a complex organic waste may be thermally treated and pumped directly into a fermenter for lactic acid production. Following fermentation, a centrifuge, e.g., decanter centrifuge, removes the bulk of insoluble impurities. Clarification is then achieved via microfiltration.

According to other embodiments, separation of insoluble impurities is carried out prior to fermentation. For example, in some embodiments, a complex organic waste may be thermally treated, subsequently enzymatically treated, and subsequently a centrifuge, e.g., a decanter centrifuge, removes the bulk of insoluble impurities. The supernatant (which still has some impurities) is pumped into a fermenter for lactic acid production. After fermentation, the broth is clarified via ceramic membrane microfiltration.

In hitherto described lactic acid fermentation processes, downstream processing methods for the separation of the lactic acid from the fermentation broth contain several steps. The first step typically involves the removal of insoluble particles (such as fat particles and oils) and the separation of cells and their debris from the fermentation broth. Microfiltration and/or centrifugation are common techniques for this step. The second step is usually product isolation or primary recovery, and its intent is to remove or separate extract components that differ greatly from the desired lactic acid product, such as salts and proteins. Common techniques for this step include ultrafiltration, solvent extraction, salt precipitation, and repulsive extraction. Further purification is often required to remove contaminants with similar physical and chemical properties. These contaminants are often the most challenging and expensive to remove. This requires sensitive and sophisticated technologies and equipment. Common techniques for this step include crystallization, distillation, nanofiltration, electrodialysis, and diverse types of chromatography (such as adsorption or ion exchange).

Water or other solvents are often considered as the main "impurities." Concentration or purification involves the removal of the bulk solvent or capture of the carboxylic acid, achieving concentration. The remaining impurities are typically removed after this step. Common techniques for this step include evaporation of water (optionally under vacuum), and/or concentrating through reverse osmosis (RO) filtration. Additional polishing steps could be applied, such as washing with appropriate solvents, solvent extraction, drying, etc.

Purification methods known in the art are typically designed for fermentation broths derived from substantially homogenous biomass-based feed streams having a relatively low content of solid impurities, and some of said methods utilize crystallization during the fermentation step and/or maintaining the lactic acid salt at a particulate state. Additionally, some of the known methods were designed for use of specific amounts of carbohydrates in the feedstock stream at the beginning of the fermentation process, resulting in specific amounts of magnesium lactate product at the end of the fermentation process. For example, U.S. Pat. No. 9,689,007 specifies that the fermentation medium should comprise at least 25 wt. % of a plant extract containing fermentable carbohydrates at the beginning of the process, and that the fermentation broth at the end of fermentation should contain at the most 9.5 wt. % magnesium lactate.

However, the known methods are not suitable or cost-effective for fermentation broths derived from more complex feedstocks, such as non-homogeneous mixed food wastes from municipal, industrial and commercial origin containing high contents of soluble and insoluble impurities. Additionally, the known methods are not suitable for fermentation broths derived from complex feedstocks having a wide range of possible initial fermentable carbohydrate concentrations, resulting in fermentation broths having a wide range of lactate concentrations.

Surprisingly, the present inventors have found a simple and economic method for obtaining high purity magnesium lactate crystals from a non-homogeneous fermentation broth obtained from complex feedstocks comprising high concentrations of soluble and insoluble impurities. Additionally, unlike other known methods, the present method can provide high purity magnesium lactate crystals based on fermentation broths having a wide variety of initial lactate concentrations. Therefore, the present method is not confined or limited by the origin of the initial organic feedstock, or by the amount of fermentable carbohydrates in the initial organic feedstock.

Thus, according to a first aspect, the present invention provides a process for the separation and purification of magnesium lactate from a fermentation broth, comprising the steps of:
  (a) providing a clarified fermentation broth from which insoluble impurities have been removed comprising magnesium lactate in a soluble form being the result of a fermentation process, the fermentation broth being at a temperature of about 45° C. to about 75° C.;
  (b) concentrating the clarified broth from step (a) to a concentration of about 150 g/L to about 220 g/L of lactate;

(c) performing at least one cooling crystallization of the concentrated clarified broth from step (b) to obtain magnesium lactate crystals; and (d) collecting the magnesium lactate crystals obtained.

In some embodiments, the process for the separation and purification of magnesium lactate from a fermentation broth, comprising the steps of:

(a) providing a fermentation broth comprising magnesium lactate in a soluble form, being the result of a fermentation process, the fermentation broth is at a temperature of about 45° C. to about 75° C.;

(b) separating insoluble impurities from said fermentation broth to obtain a clarified broth;

(c) concentrating the clarified broth from step (b) to a concentration of about 150 g/L to about 220 g/L of lactate;

(d) performing at least one cooling crystallization of the concentrated clarified broth from step (c) to obtain magnesium lactate crystals; and (e) collecting the obtained magnesium lactate crystals.

As used herein, the term "fermentable carbohydrates" refers to carbohydrates which can be fermented by a lactic acid producing microorganism during a fermentation process. As used herein, the term "lactic acid" refers to the hydroxycarboxylic acid with the chemical formula $CH_3CH(OH)CO_2H$. The magnesium salt form of lactic acid is referred to as "magnesium lactate", having the formula $Mg(LA)_2$. The term lactate can refer to the stereoisomers of lactate: L-lactate, D-lactate, or to a combination thereof. In some exemplary embodiments, the lactate is L-lactate. In other embodiments, the lactate is D-lactate.

According to some embodiments, said fermentation broth is a non-homogeneous fermentation broth. According to some embodiments, the fermentation broth is obtained from a fermentation process of organic waste feedstocks comprising soluble and insoluble impurities. The organic waste feedstock can originate from organic fractions of food waste, selected from municipal, domestic, agricultural, industrial, commercial, and hospital waste, or combinations thereof. The organic waste can additionally originate from residues ranging from animal and human excreta, vegetable and fruit residues, plants, cooked food, protein residues, slaughter waste and combinations thereof. Each possibility represents a separate embodiment of the invention. Industrial organic food waste may include factory waste such as by products, factory rejects, market returns or trimmings of inedible food portions (such as skin, fat, crusts and peels). Commercial organic food waste may include waste from shopping malls, restaurants, supermarkets, etc.

In some embodiments, the insoluble impurities comprise insoluble organic-based impurities and insoluble inorganic-based impurities.

Non-limiting examples of insoluble organic-based impurities include: microorganisms, fats, oils, lipids, aggregated proteins, bone fragments, hairs, precipitated salts, cell debris, fibers (such as fruit and/or vegetables peels), residual unprocessed food waste (such as food shells, seeds, food insoluble particles and debris), and combinations thereof. The microorganisms can include lactic acid producing microorganisms, such as but not limited to, yeasts, bacteria and fungi. Each possibility represents a separate embodiment of the invention.

Non-limiting examples of insoluble inorganic-based impurities include: plastics, glass, residues from food packaging, sand, and combinations thereof. Each possibility represents a separate embodiment of the invention.

Non-limiting examples of soluble impurities contain: water, solvents, polysaccharides, starch, cellulose, hemicellulose, lignin, salts, color components (such as tannins, flavonoids and carotenoids), and combinations thereof. Each possibility represents a separate embodiment of the invention.

In some embodiments, the soluble and insoluble impurities content of the fermentation broth is identical to the soluble and insoluble impurities content of the feedstocks for the fermentation process. In further embodiments, the soluble and insoluble impurities content of the fermentation broth is smaller by at least about 1 wt % compared to the soluble and insoluble impurities content of the feedstocks for the fermentation process. In still further embodiments, the soluble and insoluble impurities content of the fermentation broth is smaller by at least about 5 wt %, about 10 wt %, about 15 wt %, about 20 wt %, about 30 wt %, about 40 wt %, or about 50 wt % compared to the soluble and insoluble impurities content of the feedstocks for the fermentation process.

The present process can provide high purity magnesium lactate crystals based on fermentation broths having a wide variety of initial lactate concentrations. In some embodiments, the fermentation broth at step (a) comprises an initial lactate concentration of about 50 to about 120 g/L.

In some embodiments, the fermentation broth at step (a) comprises magnesium lactate in a soluble form and at least one of insoluble organic-based impurities, insoluble inorganic-based impurities and soluble impurities, as presented herein above. In further embodiments, the fermentation broth at step (a) comprises magnesium lactate in a soluble form and at least one of: insoluble organic-based impurities (such as fats, lactic acid producing microorganisms, oils, lipids, proteins, bone fragments, hairs, precipitated salts, cell debris, and residual unprocessed food waste), insoluble inorganic-based impurities (such as plastics, glass, residues from food packaging, and sand), soluble impurities (such as polysaccharides, seed fragments, salts, and various color components), and combinations thereof.

In some embodiments, the dry matter content of the fermentation broth from step (a) ranges from about 1 wt % to about 50 wt %. As used herein, the tem "dry matter" refers to the insoluble organic- and inorganic-based impurities content in the fermentation broth from step (a). In further embodiments, the dry matter content of the fermentation broth from step (a) ranges from about 5 wt % to about 30 wt %. In some exemplary embodiments, the dry matter content of the fermentation broth from step (a) ranges from about 10 wt % to about 25 wt %.

In some embodiments, at least about 50 wt % of the insoluble organic- and/or inorganic-based impurities in the fermentation broth from step (a) are in the form of particles. In further embodiments, at least about 60 wt %, about 70 wt %, about 80 wt %, about 90 wt %, or about 95 wt % of the insoluble organic- and/or inorganic-based impurities in the fermentation broth from step (a) are in the form of particles. In still further embodiments, about 100 wt % of the insoluble organic- and/or inorganic-based impurities in the fermentation broth from step (a) are in the form of particles.

In further embodiments, said insoluble organic- and/or inorganic-based particles are characterized by having a particle size in the range of about 1 μm to about 5 mm. In yet still further embodiments, said insoluble organic- and/or inorganic-based particles are characterized by having a particle size in the range of about 1 μm to about 2 mm. In still further embodiments, said insoluble organic- and/or inorganic-based particles are characterized by having a particle size in the range of about 10 µm to about 1 mm.

The term "particle size" as used herein refers to the length of the particle in the longest dimension thereof. The particles have a shape selected from spherical, non-spherical, flake, platelet, spongiform, and combinations thereof.

In some embodiments, the fermentation broth at step (a) is at a temperature selected from about 45° C. to about 75° C. In further embodiments, the fermentation broth at step (a) is at a temperature selected from about 50° C. to about 70° C. In still further embodiments, the fermentation broth at step (a) is at a temperature selected from about 55° C. to about 65° C. In yet still further embodiments, the fermentation broth at step (a) is at a temperature selected from about 55° C. to about 60° C.

In some embodiments, when the separation of insoluble impurities is carried out after fermentation, the fermentation broth during the separation process is at a temperature selected from about 45° C. to about 75° C. In further embodiments, the fermentation broth during the separation process is at a temperature selected from about 50° C. to about 70° C. In still further embodiments, the fermentation broth during the separation process is at a temperature selected from about 55° C. to about 65° C. In yet still further embodiments, the fermentation broth during the separation process is at a temperature selected from about 55° C. to about 60° C.

In some embodiments, the fermentation broth during the concentration step is at a temperature selected from about 45° C. to about 75° C. In further embodiments, the fermentation broth during the concentration step is at a temperature selected from about 50° C. to about 70° C. In still further embodiments, the fermentation broth during the concentration step is at a temperature selected from about 55° C. to about 65° C. In yet still further embodiments, the fermentation broth during the concentration step is at a temperature selected from about 55° C. to about 60° C.

In some embodiments, the fermentation broth is maintained at a temperature selected from about 45° C. to about 75° C. In further embodiments, the fermentation broth is maintained at a temperature selected from about 55° C. to about 65° C.

The process of the present invention comprises maintaining the fermentation broth at a temperature of about 45-75° C., in which the magnesium lactate is in a soluble form, until the cooling crystallization step, such that substantially no crystals are formed before the fermentation broth is clarified from the insoluble impurities and concentrated to a desired concentration. In some embodiments, less than about 5 wt % of magnesium lactate crystals are formed prior to the cooling crystallization step. In further embodiments, less than about 4 wt %, about 3 wt %, about 2 wt %, or about 1 wt % of magnesium lactate crystals are formed prior to the cooling crystallization step. Each possibility represents a separate embodiment of the present invention. In some embodiments, less than about 0.5 wt % of magnesium lactate crystals are formed prior to the cooling crystallization step.

Without wishing to be bound to any theory, it is contemplated that the removal of said insoluble impurities and the concentration of the broth should be performed at a temperature of about 45-75° C., which is above the solubility temperature of magnesium lactate, thus maintaining the magnesium lactate in a soluble form and preventing the precipitation of magnesium lactate. The present inventors have surprisingly found that the formation of magnesium lactate crystals during the fermentation process of non-homogeneous feedstocks and prior to clarification and concentration, results in low purity magnesium lactate crystals having high amounts of soluble and insoluble impurities incorporated within (such as color components), and undesired crystalloid polymorphs. Additionally, the present inventors have found that the formation of magnesium lactate crystals during clarification and/or concentration, prior to crystallization, results in low purity magnesium lactate crystals having high amounts of soluble and insoluble impurities incorporated within.

In some embodiments, the separation of insoluble particles comprises subjecting the fermentation broth containing magnesium lactate in a soluble form to a solid/liquid separation and/or to a liquid/liquid separation. In further embodiments, said solid/liquid and/or liquid/liquid separation provides clarified magnesium lactate broth and a residue comprising insoluble impurities.

In some embodiments, the solid/liquid separation comprises at least one technique selected from: filtration, centrifugation, flotation, sedimentation, flocculation and decantation. Each possibility represents a separate embodiment of the invention. In some embodiments, the liquid/liquid separation comprises at least one technique selected from: centrifugation, filtration, mixer-settlers, solvent extraction and combinations thereof. In further embodiments, the separation of insoluble particles comprises at least one technique selected from: filtration, centrifugation, flotation, sedimentation, flocculation, decantation and combinations thereof.

In some embodiments, the separation of insoluble particles comprises centrifugation.

The filtration can be selected from ultrafiltration and microfiltration. In some embodiments, the separation of insoluble particles comprises microfiltration. The microfiltration can be performed by at least one of the following methods: hollow fiber membrane, ceramic filter membrane, filter press, or other methods known in the art. Each possibility represents a separate embodiment of the invention.

In some embodiments, the separation of insoluble particles comprises centrifugation and microfiltration.

In some embodiments, the concentration is performed by: the removal of water, filtration, or by other methods known in the art. The removal of water may be performed under reduced pressure (e.g. evaporation). The filtration may comprise nanofiltration or reverse osmosis. In some embodiments, the concentration is performed by evaporation, nanofiltration, reverse osmosis, or combinations thereof.

In some embodiments, the concentration is performed in the crystallization vessel, by performing the crystallization in reduced pressure.

In some embodiments, the broth is concentrated to a concentration of about 160 g/L to about 220 g/L of lactate. In further embodiments, the broth is concentrated to a concentration of about 170 g/L to about 220 g/L of lactate. In still further embodiments, the broth is concentrated to a concentration of about 180 g/L to about 220 g/L of lactate. In further embodiments, the broth is concentrated to a concentration of about 150 g/L to about 195 g/L of lactate. In still further embodiments, the broth is concentrated to a concentration of about 155 g/L to about 190 g/L of lactate. In yet still further embodiments, the broth is concentrated to a concentration of about 160 g/L to about 185 g/L of lactate. In still further embodiments, the broth is concentrated to a concentration of about 175 g/L to about 185 g/L of lactate.

The present inventors have surprisingly found that concentrating the non-homogeneous fermentation broth to a different concentration, i.e. below about 150 g/L of lactate or above about 220 g/L of lactate, results in the formation of low purity magnesium lactate crystals during crystallization.

Said low purity magnesium lactate crystals exhibit high amounts of impurities incorporated within. Such low purity magnesium lactate crystals will require additional processing steps and machinery for their purification, and therefore are not cost effective or desirable for the separation and purification of magnesium lactate from said non-homogeneous fermentation broth, as presented herein above.

In some embodiments, before the at least one cooling crystallization, the initial pH of the concentrated clarified broth is in the range of about 6 to about 7. Depending on the initial pH of the concentrated clarified broth, the pH may be adjusted by the addition of a base or an acid.

The acid may comprise $H_2SO_4$ or other known acids in the art. The base may be selected from a caustic salt, such as but not limited to, caustic magnesium salt, caustic sodium salt, caustic potassium salt, caustic calcium salt and caustic ammonium salt. Non limiting examples of caustic salt may be selected from $MgO$, $Mg(OH)_2$, $MgCO_3$, $Mg(HCO_3)_2$, $Ba(OH)_2$, $NaOH$, $Na_2CO_3$, $NaHCO_3$, $KOH$, $K_2CO_3$, $KHCO_3$, $CaO$, $Ca(OH)_2$, $CaCO_3$, $NH_4OH$, $(NH_4)_2CO_3$. Each possibility represent a separate embodiments of the invention.

In some embodiments, the at least one cooling crystallization begins at a first temperature selected from the range of about 50 to about 75° C., which is above the solubility temperature of magnesium lactate, thus maintaining the magnesium lactate in a soluble form. In further embodiments, the at least one cooling crystallization begins at a first temperature selected from the range of about 50 to about 70° C. In still further embodiments, the at least one cooling crystallization begins at a first temperature selected from the range of about 50 to about 65° C.

In some embodiments, the at least one cooling crystallization step ends at a second temperature selected from the range of about 15 to about 0.5° C. In further embodiments, the at least one cooling crystallization step ends at a second temperature selected from the range of about 10 to about 1° C. In still further embodiments, the at least one cooling crystallization ends at a second temperature selected from the range of about 6 to about 2° C.

In some embodiments, the cooling rate of the at least one cooling crystallization is in the range of about 50 to about 0.1° C./h. In further embodiments, the cooling rate of the at least one cooling crystallization is in the range of about 10 to about 0.5° C./h. In some exemplary embodiments, the cooling rate of the at least one cooling crystallization is in the range of about 5 to about 1° C./h.

Magnesium lactate crystals are obtained during and/or after the cooling crystallization. The present inventors have found that the specific conditions of the controlled crystallization as presented herein above, i.e. the initial temperature, final temperature, pH and cooling rate, enabled the formation of high purity magnesium lactate crystals. Said high purity magnesium lactate crystals are characterized by having a densely packed configuration, which enables them to repel soluble impurities, such as color components, during the crystallization. Performing crystallization under uncontrolled conditions resulted in the formation of low purity magnesium lactate crystals.

Following the cooling crystallization, the obtained magnesium lactate crystals are collected and separated from the remaining mother liquor. The term "mother liquor" as used herein, refers to the liquid remaining after the crystallization of the magnesium lactate crystals. In some embodiments, the obtained magnesium lactate crystals are separated from the remaining liquid by a method selected from microfiltration, nanofiltration, or another method known in the art.

In some embodiments, the remaining liquid (the mother liquor) undergoes concentration, followed by at least one additional cooling crystallization, in order to obtain additional magnesium lactate crystals. In some embodiments, the conditions of the additional concentration are identical to the conditions of the first concentration step, as presented herein above. In further embodiments, the conditions of the at least one additional cooling crystallization are identical to the conditions of the first cooling crystallization.

In some embodiments, the at least one additional cooling crystallization is performed by recycling the remaining liquid (the mother liquor) back into the crystallizer, in order to obtain additional magnesium lactate crystals. In further embodiments, the at least one additional cooling crystallization is performed by placing the remaining liquid (the mother liquor) in an additional separate crystallizer, in order to obtain additional magnesium lactate crystals.

In some embodiments, the remaining liquid (the mother liquor) undergoes at least two additional cycles of concentration and cooling crystallization. In further embodiments, the remaining liquid (the mother liquor) undergoes at least 3, at least 4, at least 5, or at least 10 additional cycles of concentration and cooling crystallization. Each possibility represents a separate embodiment of the invention.

In some embodiments, the additional magnesium lactate crystals are separated from the remaining liquid (the mother liquor) by methods presented herein above. In further embodiments, the magnesium lactate crystals obtained by the first cooling crystallization are combined with the additional magnesium lactate crystals from the at least one additional cooling crystallization, thus forming combined magnesium lactate crystals. In still further embodiments, the additional magnesium lactate crystals from the additional cycles of concentration and cooling crystallization are collected and combined together with the previously obtained magnesium lactate crystals, thus forming combined magnesium lactate crystals.

In some embodiments, the process of the present invention further comprises a washing and/or purifying step, comprising washing and/or purifying the obtained magnesium lactate crystals or the combined magnesium lactate crystals. In further embodiments, the washing and/or purifying step comprises washing and/or purifying the obtained magnesium lactate crystals or the combined magnesium lactate crystals utilizing an organic solvent or an aqueous solution. In some embodiments, the organic solvent is selected from the group consisting of: ethanol, propanol, isobutanol, cyclohexane, acetone, ethyl acetate and combinations thereof. Each possibility represents a separate embodiment of the invention. The aqueous solution can comprise water.

In some embodiments, the organic solvent or the aqueous solution in the washing and/or purifying step has a specific temperature, selected from about 0.5 to about 15° C. In further embodiments, the organic solvent or the aqueous solution has a specific temperature, selected from about 0.5 to about 8° C.

In some embodiments, the washing and/or purifying step further comprises at least one polishing step, selected from extraction, microfiltration, nanofiltration, active carbon treatment, distillation, drying and grinding. In further embodiments, washing and/or purifying further comprises packaging for transportation purposes.

In some embodiments, the resulting magnesium lactate crystals, following the washing and/or purifying step, are characterized by having a high purity of over about 85 wt %. In further embodiments, the resulting magnesium lactate crystals are characterized by having a high purity of over about 90%, about 92%, about 94 wt %, about 95 wt %, about 96 wt %, about 97 wt %, about 98 wt %, or about 99 wt %. In some embodiments, the magnesium lactate crystals comprise below about 15 wt % of soluble impurities. In further embodiments, the magnesium lactate crystals comprise below about 10 wt %, about 9 wt %, about 8 wt %, about 7 wt %, about 6 wt %, about 5 wt %, about 4 wt %, about 3 wt %, about 2 wt %, or below about 1 wt % of soluble impurities.

Figure 1:
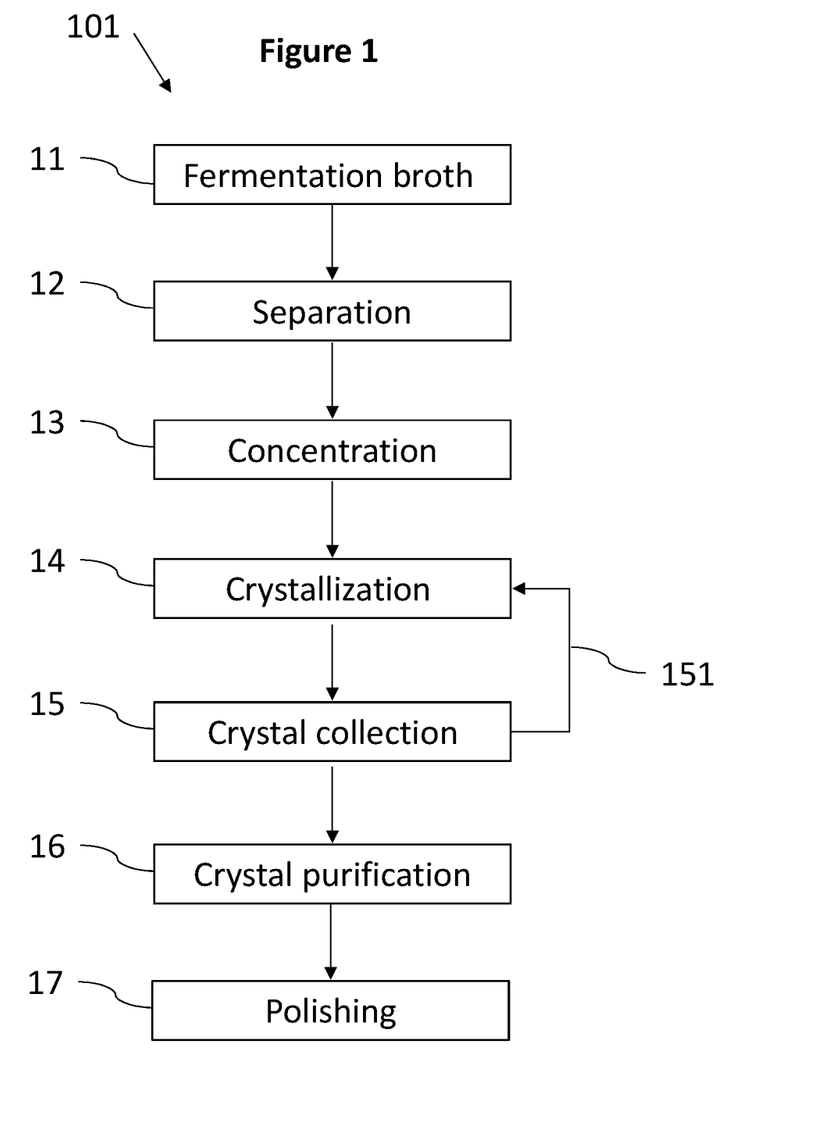
FIG. 1: depicts a schematic representation of a magnesium lactate separation and purification process according to the present invention.

Reference is now made to FIG. 1. FIG. 1 is a schematic representation of a preferred embodiment for magnesium lactate recovery and purification. Referring to FIG. 1, fermentation broth 11, which comprises magnesium lactate in a soluble form, being the result of a fermentation process, enters the magnesium lactate recovery and purification process 101. In some embodiments, the fermentation broth is maintained at a temperature of at least about 45° C. to about 75° C. Insoluble impurities, comprising insoluble organic- and inorganic-based impurities (such as particles) are separated from fermentation broth 11 utilizing a separation step 12, thus forming a clarified broth. The separation of insoluble particles from the fermentation broth at separation step 12 can utilize centrifugation and/or microfiltration.

The clarified broth is then concentrated at a concentration step 13, to a concentration of about 160 g/L to about 220 g/L of lactate, via evaporation. The concentrated broth enters a crystallization step 14, and undergoes a first crystallization in order to obtain magnesium lactate crystals. In order to obtain densely packed crystals having a high purity, the crystallization begins at a first temperature selected from the range of about 50 to about 65° C., at a cooling rate of about 5 to about 1° C./h, and ends at a second temperature selected from the range of about 5 to about 2° C. The initial pH of the clarified broth (at the beginning of the crystallization step) is in the range of about 6 to about 7.

Densely packed crystals are formed during the crystallization, which are able to repel soluble impurities, thus resulting in a high purity, for example, a purity of over 94%. Said high purity crystals comprise below about 6 wt % of soluble impurities.

At the end of the crystallization step 14 the obtained magnesium lactate crystals are separated from the remaining mother liquor at a crystal collection step 15, via filtration.

The remaining mother liquor undergoes a recycling step 151 into the crystallizer for at least one additional crystallization step 14. The magnesium lactate crystals obtained from the at least one additional crystallization are separated from the remaining mother liquor at step 15 and are combined with the crystals obtained from the first crystallization.

The combined crystals undergo a purification step 16, which comprises washing with an organic solvent selected from the group consisting of ethanol, propanol, isobutanol, cyclohexane, acetone, ethyl acetate, combinations thereof, or additional appropriate solvents known in the art.

The purified crystals undergo a final polishing step 17, said step comprises at least one additional polishing step, selected from extraction, microfiltration, nanofiltration, active carbon treatment, distillation, drying and grinding. Said additional polishing step could incorporate the preparation of the purified crystals for packaging and transportation.

The term "about" refers to ±10%, ±5%, ±1%, or ±0.1% of a specified value.

Yet, throughout the description and claims of this specification, the words "comprise" and "contain" and variations of the words, for example "comprising" and "comprises", mean "including but not limited to", and are not intended to (and do not) exclude other moieties, additives, components, integers or steps.

As used herein, the singular forms "a," "an" and "the" include plural forms unless the context clearly dictates otherwise. Thus, for example, reference to "a polysaccharide" includes combinations of polysaccharides.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Removal of Insoluble Impurities and Microfiltration

The purpose of this step is to separate insoluble impurities from the fermentation broth, in order to diminish the possibility of fouling in further downstream processing steps.

Two magnesium lactate containing fermentation broths (termed B2 and B3) were used for all of the following examples, containing different initial concentrations of lactate (Table 1 herein below). Both broths originated from commercial food waste, combining source-separated food waste from restaurants and factory rejects from bakeries. Said commercial food waste was shredded, thermally treated and underwent fermentation utilizing lactic acid—producing microorganisms. Following fermentation, each broth contained magnesium lactate, insoluble organic-based impurities, insoluble inorganic-based impurities and soluble impurities.

The broths contained about 20 wt % of insoluble impurities. The insoluble organic—and inorganic-based impurities contained particles which had an average particle size of about 1 μm to about 2 mm.

TABLE 1

| Overview of the different fermentation broths | | |
|---|---|---|
| Sample | Broth | Lactate concentration (g/L) |
| B2 | Mg(LA)$_2$ | 78.9 |
| B3 | Mg(LA)$_2$ | 85.5 |

The lactate concentration was determined using an HPLC Detector (UV-VIS and RID, Agilent 1260 Infinity).

The insoluble impurities were removed from the fermentation broths utilizing a separatory funnel and a Buchner filter (4-9 μm cardboard filters, Pall Corporation K250) attached to a vacuum pump. The temperature of the broths should be maintained at 55-60° C. during the removal of the insoluble impurities in order to maintain the magnesium lactate in a soluble form. Once clogged, filters were replaced with new filters. Microfiltration could also be conducted utilizing plate filters (Buon Vino Mini Jet Filter) having 0.5 μm cardboard membranes.

Figure 2A:
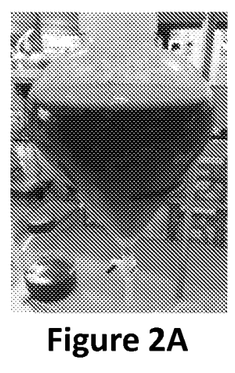
FIGS. 2A-2C: depict the separation of insoluble impurities according to some embodiments of the present invention: a separatory funnel with a magnesium lactate containing broth (FIG. 2A); Buchner filter (4 μm-9 μm cardboard filters (FIG. 2B)); and fat particles prior to their separation from the fermentation broth (FIG. 2C).
Figure 2B:
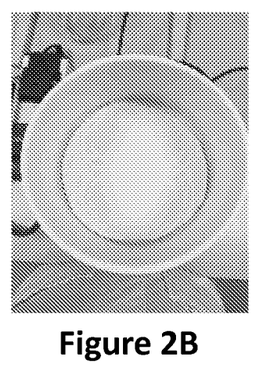
Figure 2C:
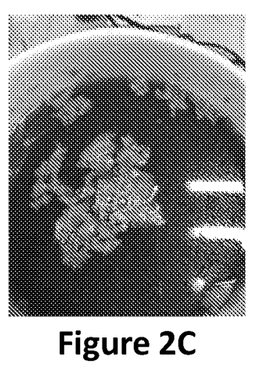

The broths initially contained a yellow oil phase (resulting from insoluble organic-based particles) that could clog the filter. The use of a separatory funnel (FIGS. 2A, 2C) prior to filtration assisted in the separation of said fat particles from the broth. This method was used for broths B2 and B3. The oil phase was present as the top layer, while the magnesium lactate aqueous solution was present as the bottom layer.

A clear, dark, and diluted lactic acid solution was obtained after filtration of the broths. The initial concentration for B2 and B3 were respectively 78.9 g/L and 85.8 g/L lactate. After filtration the concentration was 75.7 g/L lactate for B2 and 82.9 g/L lactate for B3.

Without wishing to be bound by any theory or mechanism, it is contemplated that the removal of insoluble particles (such as fat particles) before crystallization is critical, since the insoluble particles can interfere with the crystal lattice and thereby reduce the purity and change the obtained polymorphism of the lactate crystals. Additionally, it is important that the removal of these particles is performed at a temperature which is above the solubility temperature of magnesium lactate (in the above example, between 55-60° C.). Otherwise, the magnesium lactate could precipitate and damage the crystallization process.

A two-step filtration process (diafiltration) is possible in order to obtain a higher combined yield.

No traces of magnesium lactate were detected within the fat particles, indicating that there was no mass loss during the filtration.

Example 2: Concentration

The purpose of this step is to concentrate the clarified broth obtained following separation of insoluble impurities.

The clarified B2 and B3 obtained in Example 1 were concentrated to 220 g/L and 175.9 g/L of lactate, respectively.

Concentration was carried out by evaporation. The evaporation was performed at a temperature of about 60° C. utilizing a rotary evaporator (Rotavapor® R-100, Büchi). It is also possible to perform the concentration step in the crystallization vessel.

When an evaporation temperature of 80° C. was attempted, the magnesium lactate crystals obtained following crystallization were not in the preferred polymorphic form of densely packed crystals.

Without wishing to be bound by any theory or mechanism, it is contemplated that concentrated broths have better yields during crystallization. Since magnesium lactate has a solubility of 100 g/L at 20° C. (SDS of magnesium lactate, Jost Chemicals), a significant mass loss can occur in the mother liquor after crystallization by the dissolution of the magnesium lactate crystals in the mother liquor. Concentration of the saturated broth reduces the volume of the mother liquor, and thus reduces the loss of magnesium lactate. This makes evaporation necessary to obtain a reasonable process yield.

It was observed that concentrating clarified broths to concentrations below 150 g/L or above 220 g/L of lactate results in the formation of low purity magnesium lactate crystals, having an undesired spherical shape and containing high amounts of soluble impurities incorporated within (such as color components, resulting in a brown color). The yield of such a process is low.

For example, when clarified B3 was concentrated to 140 g/L of lactate, the obtained yield was 46.5%, and the obtained crystals exhibited an undesired spherical shape and a brown color, suggesting the presence of high amounts of soluble impurities incorporated within the crystals.

Example 3: Crystallization Process for Magnesium Lactate (B2)—Comparative Example Several crystallization experiments of the concentrated clarified B2 obtained in Example 2 were performed. Experiments were performed in a 500 and 2000 mL Radleys Reactor-Ready™ lab reactors, and the temperature was controlled by using a Huber Petit Fleur Thermostat.

Figure 3A:
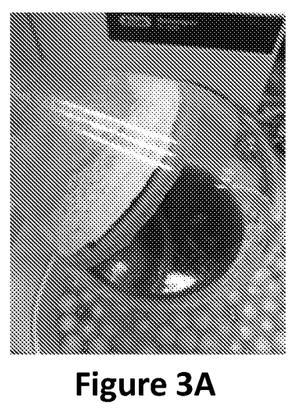
FIG. 3A-E: Crystallization of magnesium lactate (B2): precipitation of magnesium lactate on the sides of the flask (FIG. 3A); spontaneous precipitation of magnesium lactate (FIG. 3B); spherical magnesium lactate crystals (FIG. 3C); recrystallization of spherical crystals (FIG. 3D); and Buchner filtration for the separation of the fine magnesium lactate crystals (FIG. 3E).

As noted in Example 2 above, evaporation is necessary to improve the crystallization yield, in order to reduce the amount of the mother liquor which can dissolve the obtained crystals. During evaporation, precipitation of magnesium lactate on the sides of the flask is visible (FIG. 3A).

The concentrated clarified B2 obtained in Example 2 contained 220 g/L of lactate. The pH of the concentrated clarified B2 was about 7. This concentrated clarified broth was subjected to crystallization by two methods as described in the following sections.

First Method

Figure 3B:
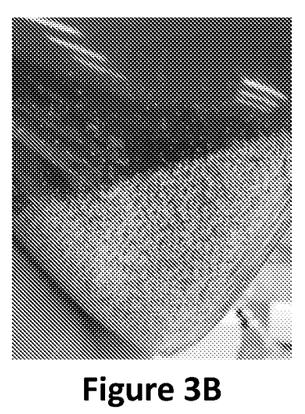
Figure 3C:
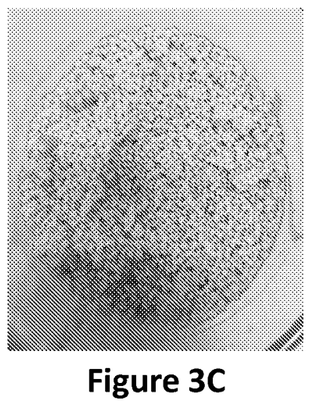
Figure 3D:
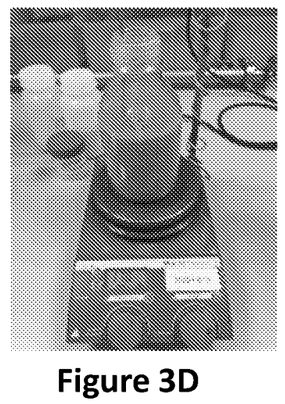
Figure 3E:
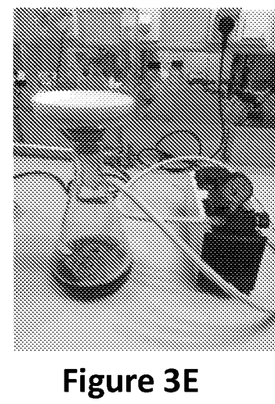

After evaporation, a first method was used for the crystallization of magnesium lactate:
1. The concentrated microfiltrate was cooled at room temperature without controlling the cooling rate. Magnesium lactate crystalized spontaneously into an undesired form of spherical crystals during cooling (FIG. 3B).
2. Part of the obtained spherical crystals from step 1 (FIG. 3C) was separated and dried at 70° C. This fraction was used for solubility determination.
3. Part of the obtained spherical crystals from step 1 was separated and underwent recrystallization by dissolving said crystals at 60° C. to a concentration of 219.8 g/L in water (FIG. 3D).
4. The solution was cooled to 16-17° C. without controlling the cooling rate.
5. The obtained Mg(LA)$_2$ crystals were separated from the mother liquor using Büchner filtration (FIG. 3E).

Results:

A total amount of 102 g of Mg(LA)$_2$ was obtained from step 5, with a dry matter content of 64.8% w/w, which corresponds with 58.8 g of lactate. The yield was 60.8%.

Second Method

Next, a second method was used for the crystallization of magnesium lactate. The same procedure as in the first crystallization method was used (steps 1-5 as in the first method), and subsequently the obtained mother liquor was concentrated and crystallized, thus allowing a higher total yield. The additional following steps were performed:
6. The mother liquor was concentrated using rotary evaporation followed by the same crystallization procedure as described above. The concentrated mother liquor was, during crystallization, cooled to 2° C.
7. The crystals from the first crystallization and from the mother liquor crystallization were dried at 70° C. and grinded into a fine powder.

Results:

A total combined process yield of 78.7% was obtained. The crystals obtained from the crystallization of the mother liquor contained more visible brown color components than the crystals obtained in the first crystallization, suggesting the presence of higher amounts of impurities incorporated within the crystals.

Example 4: Crystallization Process for Magnesium Lactate (B3)

The crystallization of concentrated clarified B3 obtained in Example 2 was regulated and controlled by using the Radleys Reactor-Ready™ lab reactor and the Huber Petit Fleur Thermostat. As noted above, the lactate concentration of concentrated clarified B3 was 175.9 g/L. The pH of concentrated clarified B3 was about 7. This concentrated clarified broth was subjected to crystallization by two methods as described in the following sections.

First Method:
1. The concentrated microfiltrate was added to the reactor at 60° C. and cooled in a controlled manner to 2° C. at a rate of 2° C./h.
2. The polymorph of the forming crystals was determined during crystallization (at 54° C., 20° C. and 2° C.) by using a polarized light microscope. Already at 54° C., the formation of Mg(LA)$_2$ crystals began, and the desired densely packed crystalloid form was obtained. During the cooling the size of the crystals increased.
3. The obtained crystals were separated from the mother liquor using Buchner filtration. The crystals at this stage had a dry mass content of 81.3% w/w.
4. Afterwards, the obtained crystals were dried at 70° C. and grinded. The dry matter content increased to 88% w/w, while the remaining 12% w/w could be attributed to residual water.
5. Additional final polishing steps are optional, such as washing the obtained crystals with suitable solvents for purification, drying and grinding.

Results:
A crystallization yield of 58.5% was obtained, which was almost the same as the yield obtained in the crystallizations of B2 (Example 3, the yield of the first method was 60.8%). Because the crystallization and the cooling process were controlled, no undesired crystal form (spherical crystals) was observed.

Second Method:
Next, a second method was used for the crystallization of magnesium lactate. The same procedure as in the first crystallization method was used (steps 1-5 as in the first method), and subsequently the obtained mother liquor was concentrated and crystallized, thus allowing a higher combined total yield, of 65.4%.

Three fractions of the crystals obtained from the initial solution were separated from the mother liquor and were used to find the most suitable washing solution or solvent. The aim of this step in the experiment was to increase the crystal purity and to remove any remaining impurities. The fractions underwent the following treatments:

Mg(LA)$_2$ crystals without washing
Mg(LA)$_2$ crystals washed with 200 mL cold ethanol (2° C.)
Mg(LA)$_2$ crystals washed with 200 mL cold water (2° C.)

Figure 4:
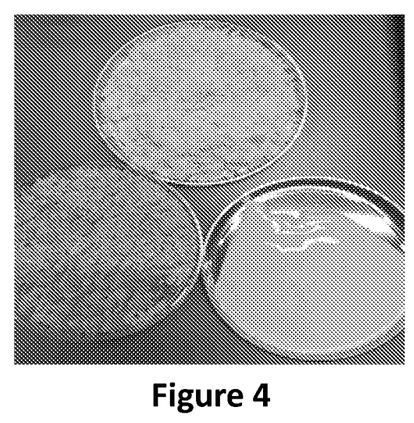
FIG. 4: Magnesium lactate crystals (B3): without washing (bottom left corner); washed with 200 mL cold ethanol (top); and washed with 200 mL cold water before drying (bottom right corner).

Results
A clear difference in color between the different fractions was visible. The crystals that were washed with water or ethanol were whiter and cleaner compared to the unwashed crystals. The crystals that were washed with water partly dissolved, and a loss of 9.9 g/L of lactate was measured in the wash water. After drying at 70° C., the crystals became solid again (FIG. 4).

Figure 5A:
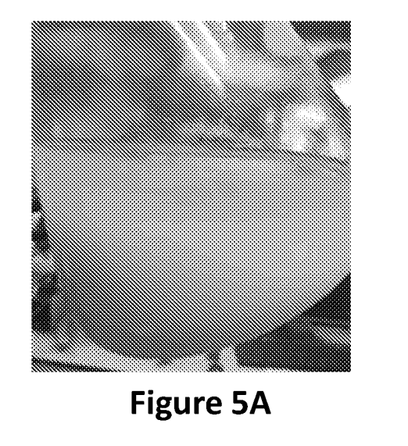
FIG. 5A-B: Filtrate obtained after washing magnesium lactate crystals (B3) with ethanol: suspension obtained after washing the crystals with ethanol (FIG. 5A); and cake after filtering the filtrate (FIG. 5B).
Figure 5B:
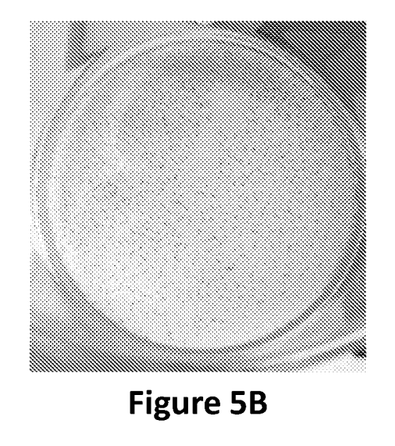

After washing the Mg(LA)$_2$ crystals with cold ethanol, the obtained filtrate (ethanol remaining after the wash) contained two fractions in a suspension form (FIG. 5A). The suspension was filtered by using a Buchner filter and a thin cake was obtained (FIG. 5B). The filtrate had a concentration of 2.9 g/L of lactate. The suspension is probably a mixture of impurities and salts which are poorly soluble in ethanol.

Figure 6:
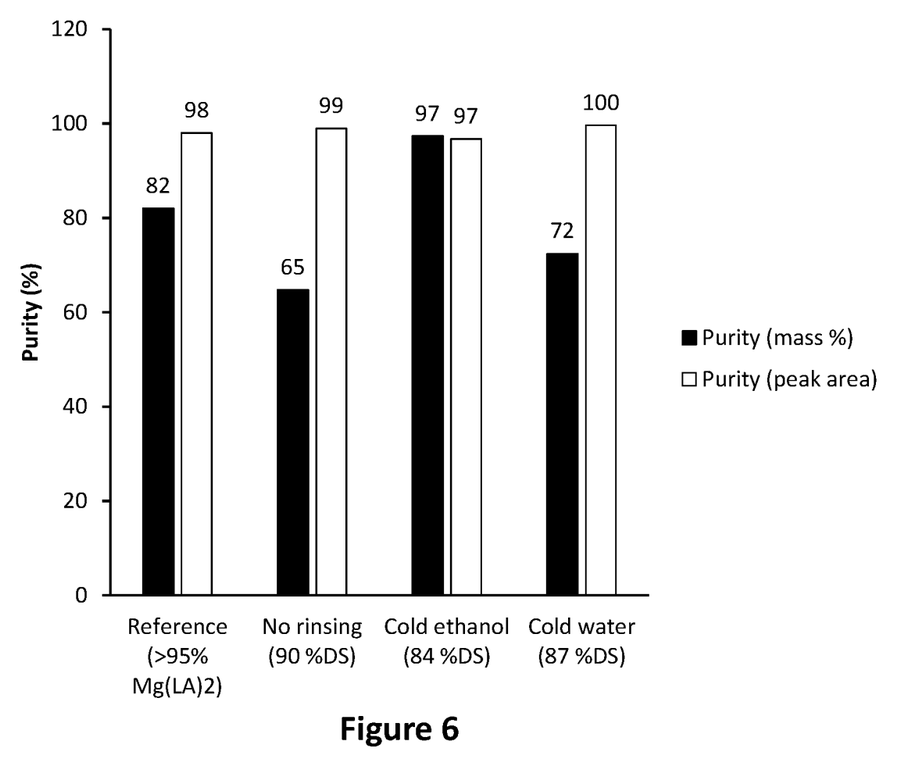
FIG. 6: Purity results of the different magnesium lactate crystal fractions (B3).

All three fractions were dried (70° C.), grinded and their purity was determined based on weight (difference between weight and measurement of the same sample on HPLC) and by quantifying the peak area. A high purity of 97% was obtained for the ethanol rinsed crystals (FIG. 6). Rinsing with water didn't have a beneficial effect on the purity (72%). The lowest purity was obtained for crystals that weren't rinsed at all (65%).

Example 5: Solubility of Magnesium Lactate for Crystallization

The purpose of this experiment is to identify a proper solubility curve as this will become a critical tool for the development of an effective crystallization process. The solubility of magnesium lactate was determined in water. The influence of temperature on solubility was evaluated by assessing the solubility at several temperatures. Three different types of Mg(LA)$_2$ samples were analyzed:
1. Mg-Lactate from Sigma-Aldrich
2. Mg-Lactate from B2 (spherical crystals, Example 3—step 2)
3. Mg-Lactate from B2 (fine crystals, after recrystallization of the spherical crystals, Example 3—steps 3-5).

The following method was used to determine the solubility of magnesium lactate in water at varying temperatures:
1. 5 mL Eppendorf tubes with water (approximately 0.5 mL) were cooled to 10° C. and placed in an Eppendorf Thermomixer.
2. An excess of dry Mg(LA)$_2$ was added and mixed for at least 2 hours.
3. Step 2 was repeated for each tube until the product would no longer dissolve.
4. The undissolved fraction was allowed to sediment, or if needed, was centrifuged briefly.
5. 20 µL of the supernatant were collected using a positive displacement pipette and diluted in 980 µL of RO water. The dilution is necessary in order to avoid recrystallization/solidification during HPLC.
6. The diluted samples were filtered using a 0.2 µm PES filter and subjected to HPLC.
7. The mg-lactate concentration was determined by HPLC.
8. The temperature was increased from 10 up to 60° C. and steps 1-6 were repeated for each temperature.

Results

Mg-Lactate from Sigma-Aldrich

Figure 7:
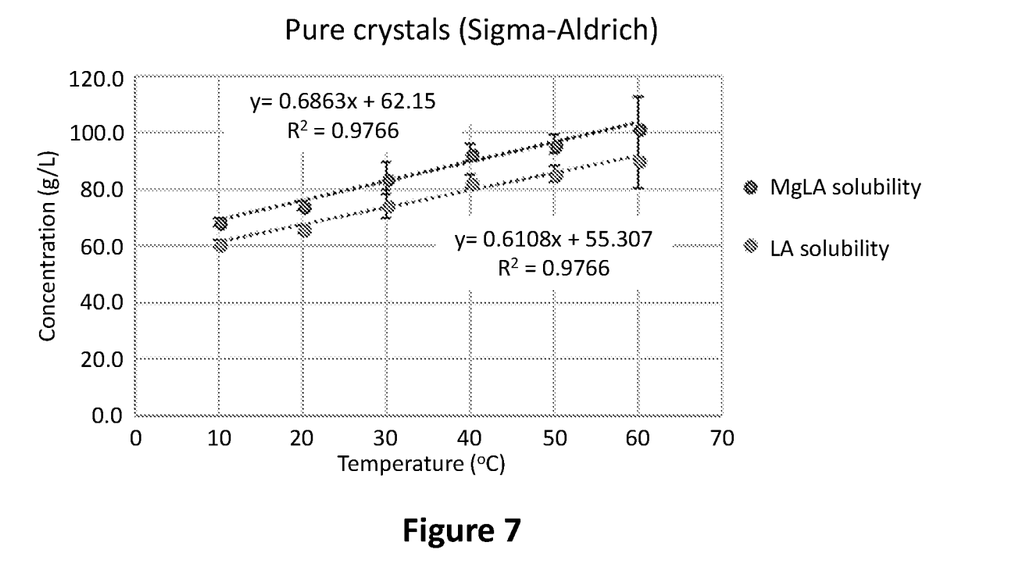
FIG. 7: Solubility curve of pure magnesium lactate crystals and lactic acid (Sigma-Aldrich).

Pure Mg(LA)$_2$ crystals from Sigma-Aldrich were analyzed (FIG. 7). The solubility at 20° C. was 74.1 g/L, which is significantly lower compared to the obtained data from the literature. The sample from Sigma-Aldrich is a mixture of anhydrous and hydrous Mg(LA)$_2$, causing a lower solubility than anhydrous Mg(LA)$_2$. An anhydrous compound from a hydrate is generally highly soluble in water than the hydrous form. An anhydrous compound can be obtained by removing the water molecules from the crystal structure.

Mg-Lactate from B2 (Spherical Crystals and Fine Powder)

Figure 8:
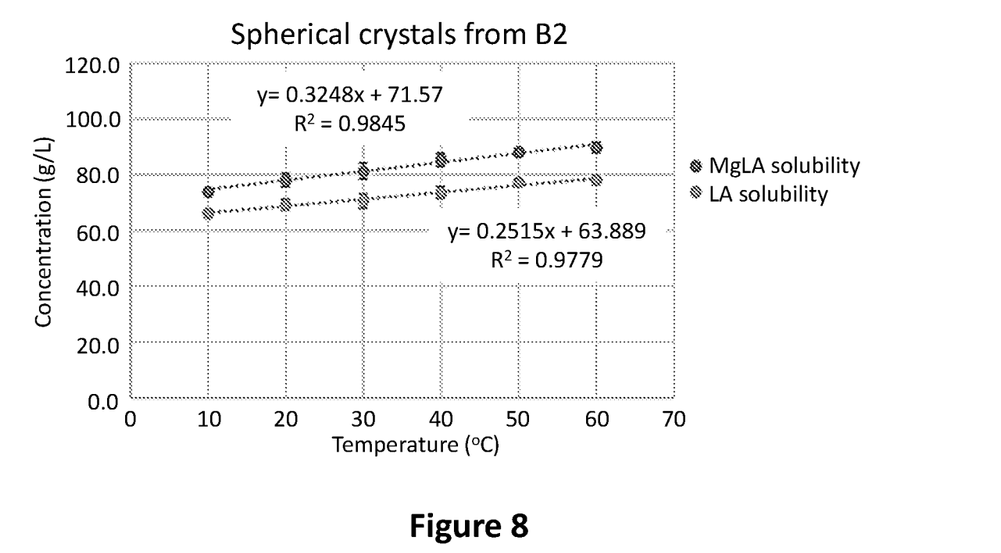
FIG. 8: Solubility curve of magnesium lactate and lactic acid (spherical crystals from B2).
Figure 9:
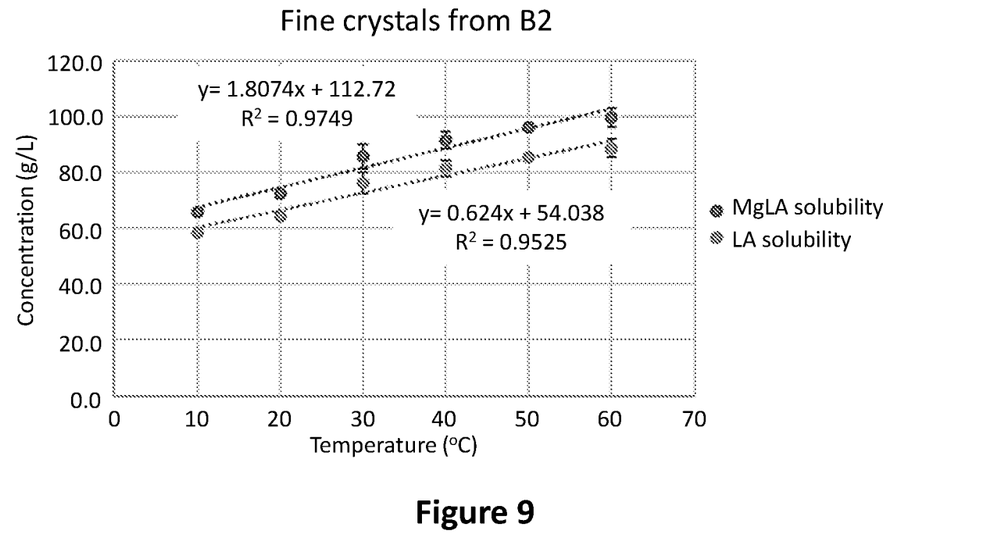
FIG. 9: Solubility curve of magnesium lactate and lactic acid (fine crystals from B2)

Two types of crystals were analyzed for the solubility in water. Spherical crystals were obtained from the precipitation of Mg(LA)$_2$ after evaporation (FIG. 8). The fine crystals (FIG. 9) were obtained after recrystallization of the spherical crystals.

Due to the different polymorphism, the solubility of the fine crystals (at 20° C.: 72.4 g/L Mg(LA)$_2$) is lower than the spherical crystals (at 20° C.: 78.2 g/L Mg(LA)$_2$). Without wishing to be bound by any theory or mechanism, it is contemplated that the most stable polymorphic form of any material is the one with the lowest chemical potential. It is possible that the spherical crystals contained some impurities, since they were formed via uncontrolled precipitation.

These impurities could get into the crystal lattice and lower the stability of the structure (influence the chemical potential).

It was found that the spherical crystals (at 60° C.: 90.0 g/L Mg(LA)$_2$) became less soluble over time than the fine Mg (LA)$_2$ crystals (at 60° C.: 99.7 g/L Mg(LA)$_2$).

Example 6: Thermogravimetric Analysis (TGA)

The purpose of this experiment is to get additional information regarding the composition of Mg(LA)$_2$ crystals after thermal degradation, and to investigate the hypothesis that the crystals produced during crystallization are in a dihydrate form (i.e. Mg(LA)$_2$·2H$_2$O).

The thermal analysis was performed using a TGA Q500 from TA instruments. The following samples were analyzed:
  Pure Mg(LA)$_2$ from Sigma Aldrich
  Mg(LA)$_2$ from B3 before washing (Example 4)
  Mg(LA)$_2$ from B3 after washing with ethanol (Example 4)

A small amount of each sample was placed on an aluminum pan. The maximum sample weight was 1 g. The heating rate was 10° C./min, ranging from 50° C. to 800° C. N$_2$ was used as a carrier gas during the TGA analysis.

Results

In the TGA thermogram of the three samples, three transitions were visibly seen (FIG. 10):
  1. Between 100° C. and 200° C.
  2. Between 325° C. and 350° C.
  3. Between 350° C. and 450° C.

Figure 10:
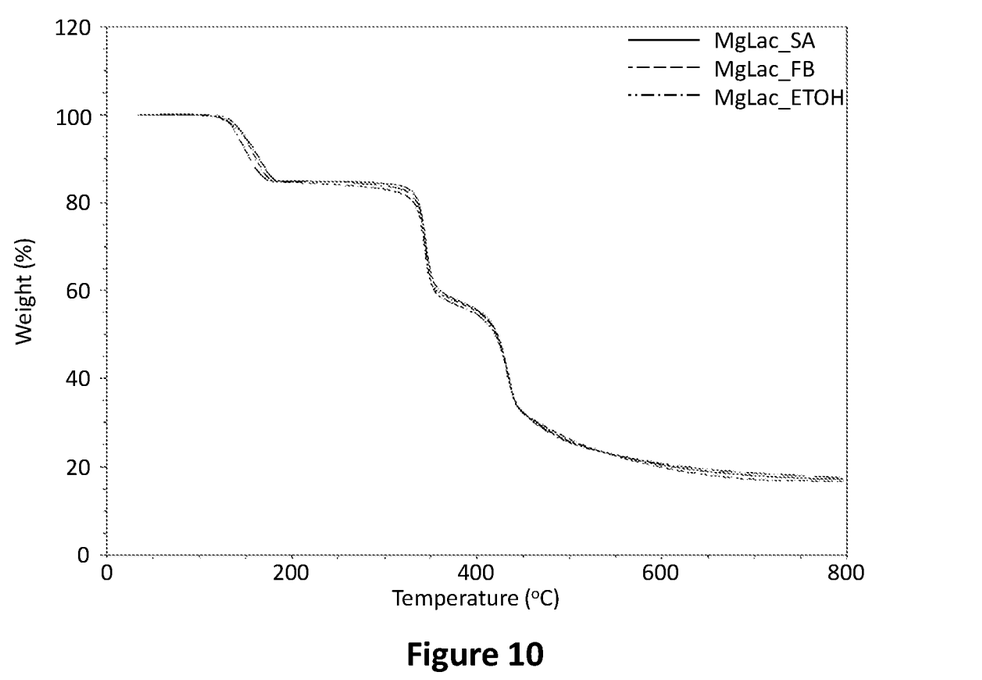
FIG. 10: TGA thermogram of three different magnesium lactate samples.

The first transition, from 100° C.-200° C., is attributed to the evaporation of unbound water and the release of hydrate water. This transition accounts for approximately 15% of the total sample weight, and is supported by the theoretical calculation, which is based on the mass of water from the mass of Mg(LA)$_2$·2H$_2$O.

$$\frac{2 \times MM_{H_2O}}{MM_{Mg(LA)_2 \cdot 2H_2O}} = \frac{36.0 \, g/mol}{238.5 \, g/mol} = 15\%$$

The second and third transitions, from 325° C.-450° C., are attributed to the combustion of lactic acid from Mg(LA)$_2$. Since the carrier gas is N$_2$, the lactic acid probably combusted into carbon and not into carbon oxides. This transition accounts for approximately 68% of the total sample weight, which was less compared to the theoretical amount of lactic acid in Mg(LA)$_2$·2H$_2$O:

$$\frac{2 \times MM_{LA}}{MM_{Mg(LA)_2 \cdot 2H_2O}} = \frac{180.2 \, g/mol}{238.5 \, g/mol} = 76\%$$

At the end of the experiment, about 17% of the total of the Mg(LA)$_2$·2H$_2$O original amount remained, which corresponds with the amount of MgO in Mg(LA)$_2$·2H$_2$O:

$$\frac{MM_{MgO}}{MM_{Mg(LA)_2 \cdot 2H_2O}} = \frac{40.3 \, g/mol}{238.5 \, g/mol} = 17\%$$

It can be concluded based on the TGA results that the produced Mg(LA)$_2$ and also the purchased sample of Sigma-Aldrich is in a dihydrate form.

Example 7: Large Scale Separation and Purification

The purpose of this experiment was to purify magnesium lactate from a fermentation broth in a large scale. The broth originated from rotted food waste, and contained residues of: bananas, oranges, apples (having plastic stickers), potatoes, cabbages, cucumbers, carrots, tomatoes, Tofu, rice, bread, milk, cheese (having 3% fat) and sunflower oil, as well as water.

Said food waste was shredded, thermally treated, and underwent fermentation utilizing lactic acid—producing microorganisms. Following fermentation, the broth contained magnesium lactate, insoluble organic-based impurities, insoluble inorganic-based impurities, and soluble impurities. The fermentation broth had a volume of approximately 1000 Liter, and contained an initial concentration of 76.3 g/L of lactate.

The insoluble impurities were removed from the fermentation broth utilizing a decanter to separate solids, subsequently by a liquid-liquid centrifuge to separate fats/oils, and finally with ceramic membrane microfiltration. The temperature of the purified broth was maintained at 55-60° C. The purified broth was then concentrated to a concentration of 216.8 g/L of lactate by evaporation, and underwent cooling crystallization under controlled conditions, similar to the crystallization conditions presented at Example 4: the concentrated purified broth was added to the crystallization reactor at 60° C. and was cooled in a controlled way to 2° C. at a rate of 2° C./h. The obtained crystals were separated from the mother liquor, washed with cold ethanol, dried and grinded. A high purity of 98.6% was obtained.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A process for the separation and purification of magnesium lactate from a fermentation broth obtained from a fermentation process of an organic waste feedstock, comprising the steps of:
  (a) providing a clarified fermentation broth from which insoluble impurities have been removed comprising magnesium lactate in a soluble form being the result of a fermentation process, the fermentation broth being at a temperature of about 45° C. to about 75° C.;
  (b) concentrating the clarified broth from step (a) to a concentration of about 150 g/L to about 220 g/L of lactate;
  (c) performing at least one cooling crystallization of the concentrated clarified broth from step (b) to obtain magnesium lactate crystals, wherein the cooling rate of the at least one cooling crystallization is in the range of about 10° C./h to about 0.5° C./h; and
  (d) collecting the magnesium lactate crystals obtained.

2. The process according to claim 1, wherein the fermentation broth at step (a) is at a temperature of about 55° C. to about 65° C.

3. The process according to claim 1, wherein the broth at step (b) is concentrated to a concentration of about 160 g/L to about 220 g/L of lactate.

4. The process according to claim 1, wherein the broth at step (b) is concentrated to a concentration of about 170 g/L to about 220 g/L of lactate.

5. The process according to claim 1, wherein the broth at step (b) is concentrated to a concentration of about 180 g/L to about 220 g/L of lactate.

6. The process according to claim 1, wherein at step (c) the at least one cooling crystallization begins at a first temperature selected from the range of about 50° C. to about 75° C.

7. The process according to claim 1, wherein at step (c) the at least one cooling crystallization begins at a first temperature selected from the range of about 50° C. to about 70° C.

8. The process according to claim 1, wherein at step (c) the at least one cooling crystallization begins at a first temperature selected from the range of about 50° C. to about 65° C.

9. The process according to claim 1, wherein at step (c) the at least one cooling crystallization step ends at a second temperature selected from the range of about 10° C. to about 1° C.

10. The process according to claim 1, wherein at step (c) the at least one cooling crystallization ends at a second temperature selected from the range of about 6° C. to about 2° C.

11. The process according to claim 1, wherein at step (c) the cooling rate of the at least one cooling crystallization is in the range of about 5° C./h to about 1° C./h.

12. The process according to claim 1, wherein at step (c) before the at least one cooling crystallization, the pH of the concentrated clarified broth is in the range of about 6 to about 7.

13. The process according to claim 1, wherein the obtained magnesium lactate crystals at step (d) are separated from the remaining liquid by a method selected from microfiltration and nanofiltration.

14. The process according to claim 13, wherein the remaining liquid from step (c) undergoes concentration, followed by at least one additional crystallization, in order to obtain additional magnesium lactate crystals, and wherein the additional obtained magnesium lactate crystals are separated from the liquid.

15. The process according to claim 14, wherein the obtained magnesium lactate crystals from step (d) are combined with the additional obtained magnesium lactate crystals obtained from the remaining liquid from step (c), thus forming combined magnesium lactate crystals.

16. The process according to claim 15, further comprising step (e), wherein step (e) comprises washing and/or purifying the obtained magnesium lactate crystals or the combined magnesium lactate crystals, utilizing an organic solvent selected from the group consisting of: ethanol, propanol, isobutanol, cyclohexane, acetone, ethyl acetate and combinations thereof.

17. The process according to claim 15, further comprising step (e), wherein step (e) comprises washing and/or purifying the obtained magnesium lactate crystals or the combined magnesium lactate crystals with an aqueous solution.

18. The process according to claim 16, wherein the organic solvent in step (e) has a specific temperature selected from about 0.5° C. to about 8° C.

19. The process according to claim 17, wherein the aqueous solution in step (e) has a specific temperature selected from about 0.5° C. to about 8° C.

* * * * *